(12) United States Patent
Kamishita et al.

(10) Patent No.: US 12,102,645 B2
(45) Date of Patent: Oct. 1, 2024

(54) FLUTICASONE FUROATE NASAL PREPARATION COMPOSITION

(71) Applicant: TOKO YAKUHIN KOGYO CO., LTD., Osaka (JP)

(72) Inventors: Taizou Kamishita, Osaka (JP); Takashi Miyazaki, Osaka (JP)

(73) Assignee: TOKO YAKUHIN KOGYO CO., LTD., Osaka (JP)

( * ) Notice: Subject to any disclaimer, the term of this patent is extended or adjusted under 35 U.S.C. 154(b) by 802 days.

(21) Appl. No.: 15/734,898

(22) PCT Filed: Jun. 7, 2019

(86) PCT No.: PCT/JP2019/022743
§ 371 (c)(1),
(2) Date: Dec. 3, 2020

(87) PCT Pub. No.: WO2019/235616
PCT Pub. Date: Dec. 12, 2019

(65) Prior Publication Data
US 2021/0236515 A1 Aug. 5, 2021

(30) Foreign Application Priority Data
Jun. 8, 2018 (JP) ................. 2018-110634

(51) Int. Cl.
| A61K 31/58 | (2006.01) |
| A61K 9/00 | (2006.01) |
| A61K 9/10 | (2006.01) |
| A61K 47/02 | (2006.01) |
| A61K 47/10 | (2017.01) |
| A61K 47/18 | (2017.01) |
| A61K 47/26 | (2006.01) |
| A61K 47/32 | (2006.01) |

(52) U.S. Cl.
CPC ............ *A61K 31/58* (2013.01); *A61K 9/0043* (2013.01); *A61K 9/10* (2013.01); *A61K 47/02* (2013.01); *A61K 47/10* (2013.01); *A61K 47/183* (2013.01); *A61K 47/186* (2013.01); *A61K 47/26* (2013.01); *A61K 47/32* (2013.01)

(58) Field of Classification Search
CPC ........ A61K 31/58; A61K 9/0043; A61K 9/10; A61K 47/02; A61K 47/183; A61K 47/186; A61K 47/26; A61K 47/32; A61K 9/107; A61K 47/38; A61K 9/12; A61P 11/02; A61P 29/00; A61P 37/08

USPC .......................................................... 514/172
See application file for complete search history.

(56) References Cited

U.S. PATENT DOCUMENTS

| 2002/0165211 A1 | 11/2002 | Biggadike et al. |
| 2003/0091512 A1 | 5/2003 | Adjei et al. |
| 2003/0199485 A1 | 10/2003 | Biggadike et al. |
| 2009/0275668 A1* | 11/2009 | Kamishita ............ A61M 11/007 514/769 |
| 2012/0255544 A1 | 10/2012 | Padilla et al. |
| 2015/0297614 A1 | 10/2015 | Ignar et al. |

FOREIGN PATENT DOCUMENTS

| CN | 101474192 | | 7/2009 |
| CN | 101474192 A | * | 7/2009 |
| EP | 0709099 | | 5/1996 |
| JP | 2006-069946 | | 3/2006 |
| JP | 4838493 B | | 10/2011 |
| JP | 2013-064022 | | 4/2013 |
| JP | 2014501779 | | 1/2014 |
| JP | 2016-502991 | | 2/2016 |
| WO | 2002/012265 | | 2/2002 |
| WO | 2012/094283 | | 7/2012 |

OTHER PUBLICATIONS

The extended European search report issued for European Patent Application No. 19814700.1, Feb. 7, 2022, 7 pages.
Office Action issued for Russian Patent Application No. 2020143142, May 30, 2022, 15 pages including English translation.
Office Action issued for Japanese Patent Application No. 2020-523205, Feb. 14, 2023, 11 pages including machine translation.
International Search Report of PCT/JP2019/022743, Jul. 9, 2019, 2 pages.
International Preliminary Report on Patentability of PCT/JP2019/022743, Dec. 8, 2020, 8 pages.
Nambiar V. et al., "Fluticasone furoate verses fluticasone propionate: a comparative study by assessment of nasal mucociliary clearance time on patients with allergic rhinitis", Int J Otorhinolaryngol Head Neck Surg. Jan. 2016; 2(1):35-39.
Eli O. Meltzer, et al., "Comparison of patient preference for sensory attributes of fluticasone furoate or fluticasone propionate in adults with seasonal allergic rhinitis: a randomized, placebo-controlled, double-blind study", Annals of Allergy, Asthma & Immunology, 104(4),2010, 331-338.
Examination report issued in Australian Patent Application No. 2019283247, Mar. 9, 2024 (3 pages).

\* cited by examiner

*Primary Examiner* — Taylor V Oh
(74) *Attorney, Agent, or Firm* — HSML P.C.

(57) ABSTRACT

The present invention relates to a pharmaceutical composition comprising fluticasone furoate and carboxy vinyl polymer.

2 Claims, No Drawings

FLUTICASONE FUROATE NASAL PREPARATION COMPOSITION

TECHNICAL FIELD

The present invention relates to a homogeneous composition comprising fluticasone furoate, and a process for preparing the composition. The present invention may be also used for treating allergic rhinitis.

BACKGROUND ART

Corticoid steroids having anti-inflammatory activity are broadly used for treating inflammatory diseases such as dermatitis, asthma, and rhinitis. Fluticasone furoate which is one of corticoid steroids is a glucocorticoid that is topically used for lowering inflammation of skin or airway, which has been already sold on the open market as a nasal drops for treating allergic rhinitis (Patent Reference 1).

Fluticasone furoate is very slightly soluble in water. In order to increase the water-solubility of fluticasone furoate to prepare nasal drops thereof for treating allergic rhinitis, it may be effective to add an organic solvent such as ethanol or an additive for increasing the solubility. Considering the administration to delicate nasal mucosa, however, it is difficult to use a stimulant organic solvent such as ethanol in nasal drops, or it is limited to choose a safe solubilizing agent having little irritating property for nasal mucosa. After all, nasal drops of fluticasone furoate were developed as an aqueous suspension and the aqueous suspension has been already sold on the open market (Allermist™ nasal spray).

When nasal drops are developed as an aqueous suspension, the selection of suspending agents used therein is important. The selection should be done considering the character of formulations. That is, the selection of suspending agents may greatly influence the suspension character such as suspension stability, redispersibility, spray-performance, retention on mucosa (viscosity), and nasal-mucosal irritation, and may also have no small influence on the efficacy or stability of nasal drops (Patent Reference 2).

In the above-mentioned commercial product Allermist nasal spray, after all, microcrystalline cellulose and carboxymethylcellulose sodium (carmellose sodium) have been used as suspending agents. However, the suspension dispersibility of the preparation is not necessarily stable, and thus the preparation contains a reminder of shaking the bottle before using. The fact that the suspension dispersibility is not stable means to influence the stability of drug-formulation or the spray-performance. And, by shaking the preparation before using, the viscosity of the preparation decreases, and such low viscosity makes it difficult to long keep the preparation in the nasal cavity. Consequently, the adverse effect on the drug efficacy has been of increasing concern.

PRIOR ART

Patent Reference

[Patent Reference 1] WO 2002/012265
[Patent Reference 2] JP 4838493 B

SUMMARY OF INVENTION

Technical Problem

One of the purposes of the present invention is to develop a pharmaceutical composition that is a nasal-spray preparation comprising poorly-water-soluble fluticasone furoate as an aqueous suspension, which does not need to be shook before using because the suspension-dispersing state is stable, and has a good retention in the nasal cavity after spray-administration.

Solution to Problem

The present inventors have extensively studied on the above problem and have found that fluticasone furoate can become a very stable unprecedented suspension-dispersing state by adding carboxy vinyl polymer which is usually used as a viscous agent or a thickener and does not belong to a general suspending agent. Based upon the new findings, the present invention has been accomplished.

The present invention may provide the following embodiments.

(Term 1) A pharmaceutical composition comprising fluticasone furoate and carboxy vinyl polymer.

(Term 2) The pharmaceutical composition of Term 1 which is an aqueous suspension.

(Term 3) The pharmaceutical composition of Term 1 or 2, which contains 0.1 to 2% (w/w) carboxy vinyl polymer.

(Term 4) The pharmaceutical composition of any one of Terms 1 to 3, which contains 0.005 to 1% (w/w) fluticasone furoate.

(Term 5) The pharmaceutical composition of any one of Terms 1 to 4, further comprising at least one suspending agent.

(Term 6) The pharmaceutical composition of Term 5, wherein the suspending agent comprises polysorbate 80.

(Term 7) The pharmaceutical composition of any one of Terms 1 to 6, further comprising at least one antiseptic agent.

(Term 8) The pharmaceutical composition of Term 7, wherein the antiseptic agent comprises benzalkonium chloride.

(Term 9) The pharmaceutical composition of Term 7 or 8, wherein the antiseptic agent comprises disodium edetate.

(Term 10) The pharmaceutical composition of any one of Terms 1 to 9, further comprising at least one tonicity agent.

(Term 11) The pharmaceutical composition of Term 10, wherein the tonicity agent comprises sodium chloride and/or glycerin.

(Term 12) The pharmaceutical composition of Term 10 or 11, which contains 0.1 to 10% (w/w) tonicity agent.

(Term 13) The pharmaceutical composition of any one of Terms 1 to 12, which is isotonic.

(Term 14) The pharmaceutical composition of any one of Terms 1 to 13, wherein the pH is 5 to 7.

(Term 15) The pharmaceutical composition of Term 14, wherein the pH is adjusted with sodium hydroxide and/or L-arginine.

(Term 16) The pharmaceutical composition of any one of Terms 2 to 15, wherein the liquid particle size of the aqueous suspension has a mean particle size of 30 to 100 μm.

(Term 17) The pharmaceutical composition of Term 15 or 16, wherein the suspending agent comprises polysorbate 80, the antiseptic agent comprises disodium edetate and benzalkonium chloride, the tonicity agent comprises glycerin and sodium chloride, and the pH adjusting agent comprises L-arginine and sodium hydroxide.

(Term 18) A nasal-spray preparation for intranasal administration, comprising the pharmaceutical composition of any one of Terms 1 to 17.

(Term 19) A method for stabilizing the suspensibility of an aqueous suspension comprising fluticasone furoate by adding carboxy vinyl polymer.

Effect of the Invention

Thanks to the discovery of the present invention, the suspensibility of a nasal-spray preparation comprising fluticasone furoate as an aqueous suspension has got stabilized a lot and it has become unnecessary to be shook before using. In addition, as the shaking before using becomes unnecessary, the problem of viscosity-decrease due to shaking has been removed. Thereby, it is expected that the drug is long kept in the nasal cavity after it is administered into the nasal cavity, and the drug efficacy is improved to be sustainable and effective.

DESCRIPTION OF EMBODIMENTS

Fluticasone furoate is the general name of 6α,9-difluoro-17β-[(fluoromethylsulfanyl) carbonyl]-11β-hydroxy-16α-methyl-3-oxoandrosta-1,4-dien-17α-yl furan-2-carboxylate whose chemical structure is shown below, which has been broadly used in the treatment of allergic rhinitis. The content of fluticasone furoate in the present preparation is 0.005 to 1% (w/w), preferably 0.025 to 0.1%.

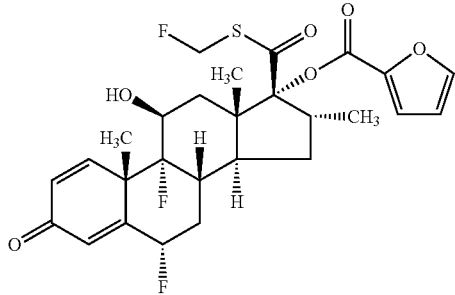

Carboxy vinyl polymer used herein should not be limited as long as it is what is usually used in a medical formulation. Preferably, it is carboxy vinyl polymer whose viscosity is adjusted by adding an outside shearing force. The method of the adjustment and the effect of the modified carboxy vinyl polymer are disclosed in WO 2007/123193. For example, the outside shearing force may be added with a known device giving a shearing force such as a high-speed spinning-type emulsifying device, a colloidal mill-type emulsifying device, a high-pressure emulsifying device, a roll mill-type emulsifying device, an ultrasonic-type emulsifying device and a membrane-type emulsifying device. Especially, a homo mixer-type, a comb-type, and an intermittently-jet-stream-generating-type, high-speed spinning-type emulsifying devices are preferable. The content of carboxy vinyl polymer is 0.1 to 2% (w/w), preferably 0.25 to 1.0%.

The suspending agent used herein includes, for example, polysorbate 80, polyoxyl 40 stearate, and/or polyoxyethylene hydrogenated castor oil 60, preferably polysorbate 80. The content of the suspending agent is 0.01 to 1% (w/w), preferably 0.025 to 0.5%.

The antiseptic agent used herein includes, for example, benzalkonium chloride, benzethonium chloride, chlorobutanol, and/or disodium edetate, preferably benzalkonium chloride and/or disodium edetate. The content of each antiseptic agent is 0.005 to 1% (w/w), preferably 0.01 to 0.02%.

Preferably, the aqueous suspension of the present invention is isotonic or around isotonic. The isotonicity may be adjusted with a tonicity agent such as sodium chloride, boric acid, glycerin and/or glucose. The content of each tonicity agent is 0.1 to 10% (w/w), preferably 0.1 to 1.0%.

The aqueous suspension of the present invention preferably has a pH of mild-acidity to around neutrality, in more detail, pH of 5 to 7. The pH may be adjusted with sodium hydroxide, potassium hydroxide, L-arginine, and the like, preferably sodium hydroxide and/or L-arginine.

The liquid particle size of sprayed aqueous suspension of the present invention is preferably a mean particle size of 30 to 100 μm, more preferably 40 to 80 μm.

The nasal-spray preparation for intranasal administration of the present invention is directed to the nasal-spray preparation in a normal nasal spray container, or in an upper-pressure-relief airless-type spray container disclosed in WO 2007/123193 and WO 2007/123207.

EXAMPLES

Hereinafter, the present invention is illustrated based on Examples, Reference examples, and Stability tests, but are not limited thereto. The evaluations of the Examples and Reference examples prepared below, and the stability tests were carried out according to Japanese Pharmacopoeia, unless otherwise indicated.

The viscosity measurement was carried out according to Japanese Pharmacopoeia/General Tests/Viscosity Determination Method II Viscosity measurement by rotational viscometer 2.1.3. Cone-flat plate-type rotational viscometer (20° ° C., 2.5 rotations per minute), and the details are as follows.

(Measuring Method)

1.1 mL of the test sample (test preparation) was charged into a sample cup of a cone-flat plate-type rotational viscometer (cone was plate type) which beforehand set for 20° C., while being careful not to put air bubble. The sample was let stand for 5 minutes, and then subjected to a shearing force for 3 minutes. Subsequently, the viscosity of the sample was measured according to the following condition.

(Measuring Condition)

Apparatus: TOKI SANGYO CO., LTD. TVE-25 type viscosity meter

Measuring range: R (full-scale torque 1437.4 μN·m)

Shearing rate: $9.575\ s^{-1}$ (2.5 rotations per minute)

Rotor: 1° 34'×R24

The liquid particle size (mean liquid particle size, 10 to 100 μm (%)) was measured by filling a nasal-spray device having a 55 mg (=50 μL)-sprayable pump with the produced preparation, spraying the preparation, and analyzing the sprayed liquid particle with a laser diffraction/scattering particle-size-distribution analyzer according to the following condition.

(Measuring Condition)

Apparatus: Malvern SprayTec

Reading distance: 30 mm

Spray angle: 40°

Extrusion speed: 100 mm/s

Example 1

(Production Method)

| Ingredients | Amount (% by weight) |
|---|---|
| fluticasone furoate | 0.05 |
| carboxy vinyl polymer | 0.56 |
| L-arginine | 0.98 |
| polysorbate 80 | 0.1 |
| disodium edatate hydrate | 0.05 |
| benzalkonium chloride | 0.01 |
| concentrated glycerin | 1.0 |
| sodium chloride | 0.5 |
| purified water | q.s. (96.75) |
| Total | 100.0 |

Carboxy vinyl polymer was dispersed, mixed, and dissolved in purified water. To the solution was added a solution of L-arginine, disodium edatate hydrate, and sodium chloride in purified water, and the mixture was stirred. A solution of benzalkonium chloride in purified water was added to the mixture, and the mixture was stirred. Separately, fluticasone furoate was wetted with concentrated glycerin, and then polysorbate 80 and purified water were added thereto. The mixture was homogeneously dispersed to prepare a homogeneous wet solution of fluticasone furoate. The wet solution of fluticasone furoate was added to the above-prepared solution comprising carboxy vinyl polymer, and the mixture was stirred to give a homogeneous nasal preparation.

(Evaluation Result)

The evaluation results of the obtained nasal preparation are shown below.

| Aspect | A white suspensible viscous liquid, which is practically odorless |
|---|---|
| pH | 6.2 |
| Viscosity (mPa · s) | 1250 |
| Osmolality (mOs/L) | 280 |
| Mean liquid particle size (μm) | 75 |
| Liquid particle size of 10 to 100 μm (%) | 81.4 |

Example 2

(Production Method)

| Ingredients | Amount (% by weight) |
|---|---|
| fluticasone furoate | 0.0275 |
| carboxy vinyl polymer | 0.52 |
| L-arginine | 0.91 |
| polysorbate 80 | 0.1 |
| disodium edatate hydrate | 0.05 |
| benzalkonium chloride | 0.01 |
| sodium chloride | 0.25 |
| ethanol | 1.0 |
| purified water | q.s. (97.1325) |
| Total | 100.0 |

A solution of L-arginine, disodium edatate hydrate, and sodium chloride in purified water was charged into a vacuum mixer, then a solution of benzalkonium chloride and polysorbate 80 in purified water was added thereto, and the mixture was stirred. Separately, carboxy vinyl polymer was dissolved in purified water with stirring and the solution was added to the mixture in the vacuum mixer. The mixture was stirred in the vacuum mixer. Separately, fluticasone furoate was wetted with concentrated glycerin, and then polysorbate 80 and purified water were added thereto. After wetting the mixture, the wet solution of fluticasone furoate was added to the stirred mixture prepared above. The mixture was stirred in the vacuum mixer. Further, the mixture was subjected to a high-speed shearing force to adjust the viscosity to 1250 mPa·s with stirring.

(Evaluation Result)

The evaluation results of the obtained nasal preparation are shown below.

| Aspect | A white suspensible viscous liquid, which is practically odorless |
|---|---|
| pH | 6.3 |
| Viscosity (mPa · s) | 1250 |
| Osmolality (mOs/L) | 265 |
| Mean liquid particle size (μm) | 67 |
| Liquid particle size of 10 to 100 μm (%) | 86.8 |

Example 3

(Production Method)

| Ingredients | Amount (% by weight) |
|---|---|
| fluticasone furoate | 0.0275 |
| carboxy vinyl polymer | 0.53 |
| L-arginine | 0.95 |
| polysorbate 80 | 0.1 |
| disodium edatate hydrate | 0.05 |
| benzalkonium chloride | 0.01 |
| concentrated glycerin | 1.0 |
| sodium chloride | 0.5 |
| purified water | q.s. (96.8325) |
| Total | 100.0 |

Carboxy vinyl polymer was dispersed, mixed, and dissolved in purified water. To the solution was added a solution of L-arginine, disodium edatate hydrate, and sodium chloride in purified water, and the mixture was stirred. A solution of benzalkonium chloride in purified water was added to the mixture, and the mixture was stirred. Separately, fluticasone furoate was wetted with concentrated glycerin, and then polysorbate 80 and purified water were added thereto. The mixture was sufficiently wetted. The wet mixture of fluticasone furoate was added to the above-prepared mixture comprising carboxy vinyl polymer, and the obtained mixture was stirred in a vacuum mixer.

(Evaluation Result)

The evaluation results of the obtained nasal preparation are shown below.

| Aspect | A white suspensible viscous liquid, which is practically odorless |
|---|---|
| pH | 6.2 |
| Viscosity (mPa · s) | 1150 |
| Osmolality (mOs/L) | 281 |

-continued

| Aspect | A white suspensible viscous liquid, which is practically odorless |
|---|---|
| Mean liquid particle size (μm) | 72 |
| Liquid particle size of 10 to 100 μm (%) | 81.5 |

Example 4

(Production Method)

| Ingredients | Amount (% by weight) |
|---|---|
| fluticasone furoate | 0.05 |
| carboxy vinyl polymer | 0.53 |
| L-arginine | 0.2 |
| polysorbate 80 | 0.1 |
| disodium edatate hydrate | 0.05 |
| benzalkonium chloride | 0.01 |
| sodium chloride | 0.035 |
| concentrated glycerin | 0.875 |
| ethanol | 0.8 |
| purified water | q.s. (97.1325) |
| Total | 100.0 |

A solution of L-arginine, disodium edatate hydrate, and sodium chloride in purified water was charged into a vacuum mixer, then a solution of benzalkonium chloride and polysorbate 80 in purified water was added thereto, and the mixture was stirred. Separately, carboxy vinyl polymer was dissolved in purified water with stirring and the solution was added to the mixture in the vacuum mixer. The mixture was stirred in the vacuum mixer. Separately, fluticasone furoate was wetted with concentrated glycerin, and then polysorbate 80 and purified water were added thereto. After wetting the mixture, the wet solution of fluticasone furoate was added to the stirred mixture prepared above. The mixture was stirred in the vacuum mixer. Further, the mixture was subjected to a high-speed shearing force to adjust the viscosity to 1000 mPa·s with stirring.

(Evaluation Result)

The evaluation results of the obtained nasal preparation are shown below.

| Aspect | A white suspensible viscous liquid, which is practically odorless |
|---|---|
| pH | 4.5 |
| Viscosity (mPa · s) | 1000 |
| Osmolality (mOs/L) | 273 |
| Mean liquid particle size (μm) | 88 |
| Liquid particle size of 10 to 100 μm (%) | 68.4 |

Example 5

(Production Method)

| Ingredients | Amount (% by weight) |
|---|---|
| fluticasone furoate | 0.05 |
| carboxy vinyl polymer | 0.35 |
| L-arginine | 0.50 |
| polysorbate 80 | 0.025 |
| disodium edatate hydrate | 0.015 |
| benzalkonium chloride | 0.01 |
| sodium chloride | 0.035 |
| concentrated glycerin | 0.875 |
| ethanol | 0.5 |
| purified water | q.s. (97.64) |
| Total | 100.0 |

A solution of L-arginine, disodium edatate hydrate, and sodium chloride in purified water was charged into a vacuum mixer, then a solution of benzalkonium chloride and polysorbate 80 in purified water was added thereto, and the mixture was stirred. Separately, carboxy vinyl polymer was dissolved in purified water with stirring and the solution was added to the mixture in the vacuum mixer. The mixture was stirred in the vacuum mixer. Separately, fluticasone furoate was wetted with concentrated glycerin, and then polysorbate 80 and purified water were added thereto. After wetting the mixture, the wet solution of fluticasone furoate was added to the stirred mixture prepared above. The mixture was stirred in the vacuum mixer. Further, the mixture was subjected to a high-speed shearing force to adjust the viscosity to 1000 mPa·s with stirring.

(Evaluation Result)

The evaluation results of the obtained nasal preparation are shown below.

| Aspect | A white suspensible viscous liquid, which is practically odorless |
|---|---|
| pH | 6.0 |
| Viscosity (mPa · s) | 1000 |
| Osmolality (mOs/L) | 275 |
| Mean liquid particle size (μm) | 75 |
| Liquid particle size of 10 to 100 μm (%) | 81.2 |

Reference Example 1 (According to Example 1 in JP 4838493 B)

(Production Method)

| Ingredients | Amount (% by weight) |
|---|---|
| fluticasone furoate | 0.05 |
| polysorbate 80 | 0.025 |
| Avicel RC591* | 1.5 |
| glucose | 5.0 |
| disodium edatate hydrate | 0.015 |
| benzalkonium chloride | 0.015 |
| 1N hydrochloric acid | q.s. |
| purified water | q.s. |
| Total | 100.0 |

*a mixture of microcrystalline cellulose and carboxymethylcellulose sodium

Glucose was dissolved in purified water to prepare a solution of glucose, and disodium edatate hydrate was added thereto and dissolved. Avicel RC591 was added to the solution with stirring to prepare a hydrated Suspension A. Separately, polysorbate 80 was dissolved in purified water at 50 to 60° ° C., and fluticasone furoate was added thereto to prepare Suspension B. Suspension A and Suspension B were mixed and stirred. To the suspension mixture was added a solution of benzalkonium chloride in purified water, and the obtained mixture was stirred. To the mixture was added 1 N hydrochloric acid to adjust the pH to 6.0. Purified water was added thereto to adjust the total weight as shown in the above table.

(Evaluation Result)

The evaluation results of the obtained nasal preparation are shown below.

| Aspect | A white opaque suspension |
| --- | --- |
| pH | 6.0 |
| Viscosity (mPa · s) | 38 |
| Osmolality (mOs/L) | 278 |
| Mean liquid particle size (μm) | 67 |
| Liquid particle size of 10 to 100 μm (%) | 84.4 |

Reference Examples 2 to 6

In the same manner, each reference example was prepared using each suspending agent shown in the table below.

| Ingredients | Example Amount (% by weight) | | | | |
| --- | --- | --- | --- | --- | --- |
| | Reference example 2 | Reference example 3 | Reference example 4 | Reference example 5 | Reference example 6 |
| fluticasone furoate | 0.05 | 0.05 | 0.05 | 0.05 | 0.05 |
| polysorbate 80 | 0.025 | 0.025 | 0.025 | 0.025 | 0.025 |
| glucose | 5.00 | 5.00 | 5.00 | 5.00 | 5.00 |
| disodium edatate hydrate | 0.015 | 0.015 | 0.015 | 0.015 | 0.015 |
| benzalkonium chloride | 0.015 | 0.015 | 0.015 | 0.015 | 0.015 |
| hydroxypropyl methylcellulose 2910*[1] | 0.55 | — | — | — | — |
| polyvinyl alcohol *[2] | — | 2.00 | — | — | — |
| sodium alginate *[3] | — | — | 1.00 | — | — |
| macrogol 4000 *[4] | — | — | — | 45.0 | — |
| chondroitin sulfate sodium *[5] | — | — | — | — | 2.00 |
| 1N hydrochloric acid | q.s. | q.s. | q.s. | q.s. | q.s. |
| 1N sodium hydroxide | q.s. | q. s. | q.s. | q.s. | q.s. |
| purified water | q.s. (up to 100%) | | | | |

*[1] to *[5] Each indicated amount is the amount of each suspending agent which was added to obtain sufficient viscosity.

(Evaluation Result)

The evaluation results of the obtained nasal preparation are shown below.

| | Reference example 2 | Reference example 3 | Reference example 4 | Reference example 5 | Reference example 6 |
| --- | --- | --- | --- | --- | --- |
| pH | 6.0 | 6.0 | 6.0 | 6.0 | 6.0 |
| Viscosity (mPa · s) | 47 | 7 | 320 | 60 | 10 |
| Spray geometry | bad (jet-like) | good (fine mist) | bad (jet-like) | bad (jet-like) | good (fine mist) |
| Mean liquid particle size (μm) | 249 | 72 | 163 | 110 | 81 |
| Liquid particle size of 10 to 100 μm (%) | 21.4 | 76.9 | 36.8 | 40.9 | 72.1 |

Stability Test 1

Using Example 5, Reference example 1, and a commercial product Allermist 27.5 μg 56 metered Nasal Spray (hereinafter, referred to as "Allermist nasal spray"), the following test was carried out.

(Test Method)

The test sample (test preparation) is sufficiently stirred and then the assay sample is taken from the test sample in homogeneous state. The content of fluticasone furoate in the assay sample is determined by high-performance liquid chromatography to give each initial content in homogeneous state (Content A).

Then, 12 g of each test sample in homogeneous state is put into a 13.5 mL glass screw-capped-bottle, and the bottle is well shook again to be in homogeneous state. The bottled test sample is left to stand at ambient temperature for 24 hours or for a week. Separately, the freshly-prepared test sample is centrifuged (5000 rpm, 10 minutes).

Before and after putting the sample into the screw-capped-bottle and shaking it, after 24-hour and one-week leaving to stand, and after centrifuging the sample, the sample in each state is evaluated about the aspect and the content of fluticasone furoate. In determining the content, each test sample is divided into an upper layer (3 g), a middle layer (4 g), and the left lower layer (3 g). Each 2 g of the upper and lower layers is weighed as assay samples, and each content of fluticasone furoate is determined by high-performance liquid chromatography (Content B). The suspension stability is evaluated based on the rate of suspension stability which can be given through the following formula.

Rate of suspension stability (%)=(Content $B$)/(Content $A$)×100

(Test Result)
Change in Aspect

|  |  | Example 5 | Reference example 1 | Allermist nasal spray |
|---|---|---|---|---|
| before shake | upper layer | No phase separation between upper layer and lower layer. | No phase separation between upper layer and lower layer. | No phase separation between upper layer and lower layer. |
|  | lower layer | A white semi-transparent viscous suspension. | A white semi-transparent viscous suspension. | A white semi-transparent viscous suspension. |
| immediately after shake | upper layer | No phase separation between upper layer and lower layer. | No phase separation between upper layer and lower layer. | No phase separation between upper layer and lower layer. |
|  | lower layer | A white semi-transparent viscous suspension. | A white semi-transparent viscous suspension. | A white semi-transparent viscous suspension. |
| 24 hours after shake | upper layer | No phase separation between upper layer and lower layer. | A white opaque suspension. | A white opaque suspension. |
|  | lower layer | A white semi-transparent viscous suspension. | A white opaque suspension. There was a small amount of precipitate at the vessel bottom. | A white opaque suspension. There was a small amount of precipitate at the vessel bottom. |
| one week after shake | upper layer | No phase separation between upper layer and lower layer. | A white opaque suspension. | A white opaque suspension. |
|  | lower layer | A white semi-transparent viscous suspension. | A white opaque suspension. There was a precipitate at the vessel bottom. | A white opaque suspension. There was a precipitate at the vessel bottom. |
| centrifugation (5000 rpm, 10 min) after shake | upper layer | No phase separation between upper layer and lower layer. | A white opaque suspension. | A white opaque suspension. |
|  | lower layer | A white semi-transparent viscous suspension. | A white opaque suspension. There was a volume of precipitate at the vessel bottom. | A white opaque suspension. There was a volume of precipitate at the vessel bottom. |

Suspension Stability

|  |  | Example 5 | Reference example 1 | Allermist nasal spray |
|---|---|---|---|---|
| immediately after well stirring | upper layer | 100.5% | 100.9% | 101.2% |
|  | lower layer | 100.3% | 100.7% | 101.8% |
| 24 hours after shake | upper layer | 100.1% | 101.4% | 101.4% |
|  | lower layer | 100.8% | 100.2% | 101.0% |
| one week after shake | upper layer | 100.3% | 97.7% | 98.4% |
|  | lower layer | 100.6% | 104.0% | 102.2% |
| centrifugation (5000 rpm, 10 min) after shake | upper layer | 100.2% | 77.3% | 88.4% |
|  | lower layer | 100.5% | 105.3% | 107.6% |

Stability Test 2

Using Example 4 and Reference examples 2 to 6, the same test as Stability test 1 was carried out, in which the assay frequency was more than that of Stability test 1. The results are shown below.

Change in Aspect

|  |  | Example 4 | Reference example 2 | Reference example 3 | Reference example 4 | Reference example 5 | Reference example 6 |
|---|---|---|---|---|---|---|---|
| before shake | upper layer | No phase separation between upper layer and lower layer. | A semi-transparent suspensible liquid | A transparent liquid | A white semi-transparent viscous suspension. | A semi-transparent suspensible liquid | A transparent liquid |
|  | lower layer | A white semi-transparent viscous suspension. | There was a small amount of precipitated crystal at the vessel bottom. | There was a precipitated crystal at the vessel bottom. | There was a slight amount of precipitated crystal at the vessel bottom. | There was a small amount of precipitated crystal at the vessel bottom. | There was a precipitated crystal at the vessel bottom. |
| immediately after shake | upper layer | No phase separation between upper layer and lower layer. | No phase separation between upper layer and lower layer. | No phase separation between upper layer and lower layer. | No phase separation between upper layer and lower layer. | No phase separation between upper layer and lower layer. | No phase separation between upper layer and lower layer. |
|  | lower layer | A white semi-transparent viscous suspension. | A white semi-transparent viscous suspension. | A white semi-transparent viscous suspension. | A white semi-transparent viscous suspension. | A white semi-transparent viscous suspension. | A white semi-transparent viscous suspension. |
| 3 hours after shake | upper layer | No phase separation between upper layer and | A semi-transparent suspensible liquid | A semi-transparent suspensible liquid | No phase separation between upper layer and | A semi-transparent suspensible liquid | A transparent liquid |

-continued

| | | Example 4 | Reference example 2 | Reference example 3 | Reference example 4 | Reference example 5 | Reference example 6 |
|---|---|---|---|---|---|---|---|
| | lower layer | lower layer. A white semi-transparent viscous suspension. | There was a small amount of precipitated crystal at the vessel bottom. | There was a precipitated crystal at the vessel bottom. | lower layer. A white semi-transparent viscous suspension. | There was a small amount of precipitated crystal at the vessel bottom. | There was a precipitated crystal at the vessel bottom. |
| 6 hours after shake | upper layer | No phase separation between upper layer and lower layer. | A semi-transparent suspensible liquid | A transparent liquid | No phase separation between upper layer and lower layer. | A semi-transparent suspensible liquid | A transparent liquid |
| | lower layer | A white semi-transparent viscous suspension. | There was a small amount of precipitated crystal at the vessel bottom. | There was a precipitated crystal at the vessel bottom. | A white semi-transparent viscous suspension. | There was a small amount of precipitated crystal at the vessel bottom. | There was a precipitated crystal at the vessel bottom. |
| 24 hours after shake | upper layer | No phase separation between upper layer and lower layer. | A semi-transparent suspensible liquid | A transparent liquid | A white semi-transparent viscous suspension | A semi-transparent suspensible liquid | A transparent liquid |
| | lower layer | A white semi-transparent viscous suspension. | There was a small amount of precipitated crystal at the vessel bottom. | There was a precipitated crystal at the vessel bottom. | There was a slight amount of precipitated crystal at the vessel bottom. | There was a small amount of precipitated crystal at the vessel bottom. | There was a precipitated crystal at the vessel bottom. |
| one week after shake | upper layer | No phase separation between upper layer and lower layer. | A semi-transparent suspensible liquid | A transparent liquid | A white semi-transparent viscous suspension | A semi-transparent suspensible liquid | A transparent liquid |
| | lower layer | A white semi-transparent viscous suspension. | There was a precipitated crystal at the vessel bottom. | There was a precipitated crystal at the vessel bottom. | There was a slight amount of precipitated crystal at the vessel bottom. | There was a precipitated crystal at the vessel bottom. | There was a precipitated crystal at the vessel bottom. |
| centrifugation (5000 rpm, 10 min) after shake | upper layer | No phase separation between upper layer and lower layer. | A semi-transparent suspensible liquid | A transparent liquid | A white semi-transparent viscous suspension | A transparent liquid | A transparent liquid |
| | lower layer | A white semi-transparent viscous suspension. | There was a precipitated crystal at the vessel bottom. | There was a precipitated crystal at the vessel bottom. | There was a small amount of precipitated crystal at the vessel bottom. | There was a precipitated crystal at the vessel bottom. | There was a precipitated crystal at the vessel bottom. |

| Suspension Stability | | Example 4 | Reference example 2 | Reference example 3 | Reference example 4 | Reference example 5 | Reference example 6 |
|---|---|---|---|---|---|---|---|
| immediately after well stirring | upper layer | 100.3% | 99.3% | 96.2% | 98.7% | 100.5% | 101.6% |
| | lower layer | 100.8% | 100.1% | 101.9% | 100.1% | 99.2% | 100.1% |
| 24 hours after shake | upper layer | 100.5% | 20.5% | 1.4% | 98.4% | 33.8% | 2.3% |
| | lower layer | 99.8% | 178.3% | 209.7% | 99.8% | 170.6% | 194.8% |
| one week after shake | upper layer | 100.5% | 18.4% | 0.6% | 97.1% | 6.8% | 1.2% |
| | lower layer | 100.1% | 188.6% | 199.2% | 104.3% | 192.7% | 199.0% |
| centrifugation | upper layer | 99.7% | 1.4% | 0.3% | 91.4% | 5.4% | 0.9% |

-continued

| | | Example 4 | Reference example 2 | Reference example 3 | Reference example 4 | Reference example 5 | Reference example 6 |
|---|---|---|---|---|---|---|---|
| (5000 rpm, 10 min) after | lower layer | 99.3% | 204.6% | 221.0% | 108.2% | 200.4% | 201.7% |

Suspension Stability

The invention claimed is:

1. A method for stabilizing a suspensibility of an aqueous suspension comprising fluticasone furoate by adding carboxy vinyl polymer.

2. The method of claim 1, wherein the aqueous suspension is prepared as a nasal-spray preparation for intranasal administration.

* * * * *